United States Patent [19]
Abou-Gharbia et al.

[11] Patent Number: 4,766,215
[45] Date of Patent: Aug. 23, 1988

[54] HISTAMINE H$_1$-RECEPTOR ANTAGONISTS

[75] Inventors: Magid A. Abou-Gharbia, Wilmington, Del.; Usha R. Patel, Audubon, Pa.

[73] Assignee: American Home Products Corporation, New York, N.Y.

[21] Appl. No.: 19,730

[22] Filed: Feb. 27, 1987

[51] Int. Cl.$^4$ ................ C07D 403/04; C07D 401/12; A61K 31/495
[52] U.S. Cl. .................... 544/357; 544/408; 544/295; 544/316; 544/335; 544/336
[58] Field of Search ............... 544/316, 335, 336, 408, 544/357, 295

[56] References Cited
U.S. PATENT DOCUMENTS

| | | | |
|---|---|---|---|
| 2,979,508 | 4/1961 | Janssen | 544/360 |
| 2,985,657 | 5/1961 | Janssen | 544/295 |
| 4,550,116 | 10/1985 | Soto et al. | 514/327 |
| 4,605,655 | 8/1986 | Yevich et al. | 544/295 |

FOREIGN PATENT DOCUMENTS

| | | | |
|---|---|---|---|
| 697941 | 11/1964 | Canada | 544/295 |
| 1294720 | 11/1972 | United Kingdom | 544/295 |
| 2120669 | 12/1983 | United Kingdom | |

OTHER PUBLICATIONS

Patel, Chem. Abstracts, vol. 75, (1971), entry 31808x.
Sonurlikar et al., Chem. Abstracts, vol. 89, (1978), entry 141166u.
Vadadaria et al., Chem. Abstracts, vol. 71, (1969), entry 101817t.
Merck Index, 9th ed., (1976), p. 170, entry #912.

Primary Examiner—Donald G. Daus
Assistant Examiner—William A. Teoli, Jr.
Attorney, Agent, or Firm—Richard K. Jackson

[57] ABSTRACT

The compounds of the following formula are histamine H$_1$-receptor antagonists:

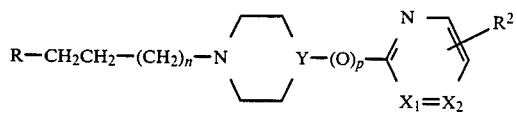

in which

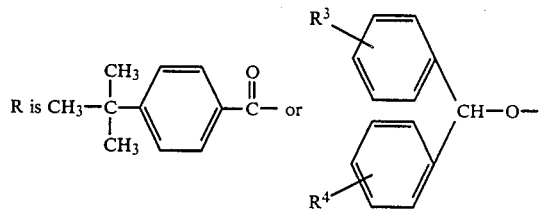

where
R$^3$ and R$^4$ are, independently, hydrogen, halo, alkoxy of 1 to 3 carbon atoms or alkyl of 1 to 3 carbon atoms; R$^2$ is hydrogen or halo;
n is one of the integers 0, 1 or 2;
p is one of the integers 0 or 1;
Y is —N= or —CH=, with the proviso that when Y is —N=, p is zero, and when Y is —CH=, p is one; and
one of X$_1$ and X$_2$ is nitrogen and the other is —CH=; or a pharmaceutically acceptable salt thereof.

4 Claims, No Drawings

HISTAMINE H₁-RECEPTOR ANTAGONISTS

BACKGROUND OF THE INVENTION

Soto et al., in U.S. Pat. No. 4,550,116 granted Oct. 29, 1985, discloses histamine $H_1$-receptor antagonists which also possess calcium antagonist activities of the formula:

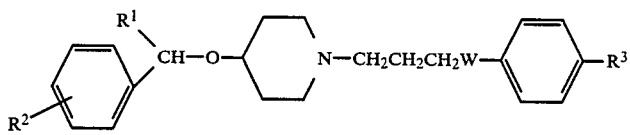

where $R^1$ is thienyl, phenyl or substituted phenyl; and
W is hydroxymethylene or a carbonyl group.

Mauri et al., —G.B. No. 2,120,669—is quite similar to the disclosure of Soto et al., although $R^1$ may also be cycloalkyl or cycloalkenyl and W is fixed as a hydroxyalkylene group. These compounds are antihistaminic agents with vasodilator properties.

DESCRIPTION OF THE INVENTION

In accordance with this invention there is provided a group of histamine $H_1$-receptor antagonists of the formula:

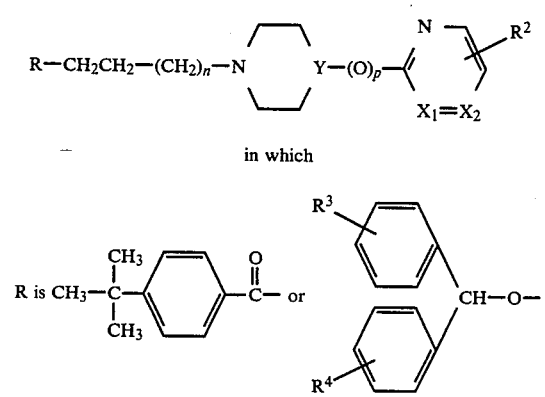

in which where
$R^3$ and $R^4$ are, independently, hydrogen, halo, alkoxy of 1 to 3 carbon atoms or alkyl of 1 to 3 carbon atoms; $R^2$ is hydrogen or halo;
n is one of the integers 0, 1 or 2;
p is one of the integers 0 or 1;
Y is —N= or —CH=, with the proviso that when Y is —N=, p is zero, and when Y is —CH=, p is one; and
one of $X_1$ and $X_2$ is nitrogen and the other is —CH=;
or a pharmaceutically acceptable salt thereof.

Within this group of compounds, the preferred variables are where n is 1; Y is nitrogen; p is zero; $X_1$ is —CH=; and $R^2$ is a halogen (e.g. chlorine, bromine, iodine, or fluorine; most preferably chlorine).

The pharmaceutically acceptable salts of the histamine $H_1$-receptor antagonists of this invention are prepared by conventional means with inorganic or organic acids such as hydrochloric, hydrobromic, sulfuric, phosphoric, nitric, acetic, fumaric, citric, tartaric, maleic, lactic, 2-hydroxyethanesulfonic, methanesulfonic, toluene-4-sulfonic, ethanesulfonic acid, and the like.

The compounds of this invention may be prepared by a variety of synthetic routes which involve conventional methods. For example, the compounds containing a piperazine ring are produced simply by alkylation of optionally substituted N-(pyrazinyl)piperazine with the appropriately substituted alkyl halide in dimethylformamide and in the presence of an acid acceptor such as triethylamine. In similar fashion, the compounds containing the piperidine ring are prepared by reaction of 2,6-dihalopiperazine with 4-hydroxypiperidine in dimethylformamide with $NaHCO_3$ as the acid acceptor to obtain the 4-(pyrazinyloxy)piperidine ether followed by N-alkylation with the appropriately substituted alkyl halide.

The following examples illustrate the preparation of representative compounds of this invention.

EXAMPLE 1

1-[3-(tert-butylbenzoyl)propyl]-4-(6-chloro-2-pyrazinyl)piperazine

To a stirred solution of p-tert-butyl-ω-chlorobutyrophenone (3 g., 0.0125 mol) in 100 ml of dimethylformamide, 2.5 g. (0.025 mol) of triethylamine and 2.95 g. (0.0125 mol) of 1-(6-chloro-2-pyrazinyl)piperazine hydrochloride were added. The reaction mixture was stirred overnight and the solvent was removed under reduced pressure. The residue was partitioned between methylene chloride and water. The methylene chloride extracts were combined, dried over anhydrous sodium sulfate, filtered and removed on a rotary evaporator to yield 7.0 g. of the crude free base which was purified by preparative HPLC (silica gel/ethyl acetate) to afford 1.2 g. of the title compound. The hydrochloride salt was formed by treating the free base with ethanolic hydrogen chloride and recrystallized from ethanol to give the monohydrochloride salt; m.p. 208°–210° C.

Analysis for: $C_{22}H_{29}N_4OCl.HCl$. Calculated: C, 60.41; H, 6.86; N, 12.81. Found: C, 60.29; H, 6.92; N, 12.82.

EXAMPLE 2

4-[4-(3-chloro-2-pyrazinyl)-1-piperazinyl]-1-[4-(1,1-dimethylethyl)phenyl]-1-butanone To a stirred solution of p-tert-butyl-ω-chlorobutyrophenone (4 g., 0.016 mol) in 100 ml. of dimethylformamide, 2.5 g. (0.025 mol) of triethylamine and 3.3 g. (0.016 mol) of 1-(3-chloro-2-pyrazinyl)piperazine were added. The reaction mixture was stirred overnight and the solvent was removed under reduced pressure. The residue was partitioned between methylene chloride and water. The methylene chloride extracts were combined, dried over anhydrous sodium sulfate, filtered and removed on a rotary evaporator to yield 6 g. of the crude free base which was purified by preparative HPLC (silica gel/ethyl acetate) to afford 2 g. (30% yield) of the title compound. The hydrochloride salt was formed by treating the free base with ethanolic hydrogen chloride and recrystallized from ethanol to give the monohydrochloride; m.p. 220°-222° C.

Analysis for: $C_{22}H_{29}N_4OCl.HCl$. Calculated: C, 60.41; H, 6.86; N, 12.81; Cl, 16.24. Found: C, 60.21; H, 6.95; N, 12.82; Cl, 15.86.

EXAMPLE 3

2-[4-[3-(diphenylmethoxy)propyl]-1-piperazinyl]-pyrimidine

To a stirred solution of 1-(2-pyrimidinyl)-4-piperazinyl propanol 3 g. (0.013 mol) in 50 mol. of dimethylformamide was added 3.3 g. (0.013 mol) of diphenylmethylbromide and 2.9 g. (0.034 mol) of sodium bicarbonate. The reaction mixture was refluxed overnight, dimethylformamide was evaporated under reduced pressure, and the residue was extracted with methylene chloride (400 ml.). The methylene chloride extracts were collected, washed with water and evaporated, and the remaining residue was purified by HPLC to give 1.3 g. (26% yield) of the title compound. The free base which was converted to the (1:1) fumarate salt; m.p 166°-168° C.

Analysis for: $C_{24}H_{28}N_4O.C_4H_4O_4$. Calculated: C, 66.66; H, 6.35; N, 11.11. Found: C, 66.75; H, 6.39; N, 10.98.

EXAMPLE 4

2-[4-[3-[bis(4-fluorophenyl)methoxy]propyl]-1-piperazinyl]-6-chloropyrazine

To a stirred solution of 1-(6-chloro-2-pyrazinyl)-4-piperazinyl propanol 3 g. (0.013 mol) in 50 ml. of dimethylformamide was added 3.3 g. (0.017 mol) of bis(4-fluorophenyl)methylbromide and 2.6 g. (0.034 mol) of sodium bicarbonate. The reaction mixture was refluxed overnight, dimethylformamide was evaporated under vacuum and the residue was extracted with methylene chloride (3×400 ml.). The methylene chloride extracts were collected, washed with water and dried (anhydrous $Na_2SO_4$). Evaporation of the methylene chloride afforded the title compound as a brown oil. HPLC purification afforded 2 g. (37% yield) of the pure product. It was converted to the (1:1) fumarate salt and recovered as the hemihydrate; m.p. 165°-167° C.

Analysis for: $C_{24}H_{25}N_4F_2ClO.C_4H_4O_4.\frac{1}{2}H_2O$. Calculated: C, 57.58; H, 5.05; N, 9.59. Found: C, 57.70; H, 5.05; N, 9.50.

EXAMPLE 5

4-[4-(6-chloro-2-pyrazinyl)oxy]-1-piperidinyl-1-[4-(1,1-dimethylethyl)phenyl]-1-butanone 4-(1,1-dimethylethyl)phenyl-ω-chlorobutyrophenone (3.0 g., 0.013 mol), 4-hydroxypiperidine (1.3 g., 0.013 mol) and $NaHCO_3$ (2.0 g., 0.024 mol) were stirred in DMF (50 ml.) at 140° C. overnight. The mixture was then refluxed for an additional day. The dimethylformamide was evaporated under reduced pressure. The residue was insoluble in water and $CH_2Cl_2$ was dissolved in aqueous HCl. The solution was filtered and the separated solid was discarded. The filtrate was basified with aqueous NaOH and the solution was extracted with $CH_2Cl_2$. The extracts were combined and dried with $MgSO_4$. The solvent was evaporated and the residue was purified by HPLC to give 1-[4-(1,1-dimethylethyl)phenyl]-4-[hydroxy-1-piperidinyl]-1-butanone 2.0 g. (0.006 mol) and 3,6-dichloropyrazine (1.03 g., 0.006 mol) were added to a suspension of $NaHCO_3$ (1.4 g., 0.017 mol) in dimethylformamide (60 ml.) and the reaction mixture was refluxed overnight. The dimethylformamide was evaporated under reduced pressure was dissolved in $CH_2Cl_2$ and $H_2O$. The aqueous layer was extracted with $CH_2Cl_2$ and the combined $CH_2Cl_2$ extracts were dried with anhydrous $MgSO_4$. The solvent was evaporated under reduced pressure and the residue was purified by HPLC to give the title compound which was converted to the (1:1) fumarate salt; m.p. 208°-210° C.

Analysis for: $C_{23}H_{30}N_3O_2Cl.C_4H_4O_4$. Calculated: C, 60.96; H, 6.39; N, 7.9. Found: C, 60.82; H, 6.59; N, 8.15.

The compounds of this invention were established to be histamine $H_1$-antagonists by subjecting them to the following standard test procedures for $H_1$-blocking activity:

Fresh segments of terminal ileum immediately proximal to Peyer's patch, obtained from male Buckshire guinea pigs, were suspended in 37° C. Tyrode's solution in a tissue bath and aerated. The tissue segments were placed under one gram tension and allowed to equilibrate for one hour. Histamine was added to each tissue bath to a final concentration of $1 \times 10^{-6}M$. The contraction response after it equilibrated was noted as grams tension. Test drug was added, in the presence of histamine, to each bath to a final concentration of $1 \times 10^{-7}M$. The change in grams tension was noted and the percent reduction in grams tension calculated.

Following this procedure, with quadruplicate sets of tissues, the compound of Example 1 demonstrated 32 percent reduction in tissue contraction and the compounds of the other examples demonstrated between 7 to 25 percent reduction in contraction.

The pharmacological results obtained characterize the compounds of this invention as $H_1$-receptor antagonists useful in the treatment of mammals experiencing conditions such as asthma, hay fever, allergic rhinitis, atopic dermatitis, conjunctivitis, pruritis, and eczema, or other responses where histamine is released and acts on $H_1$ receptors. As such, they may be administered topically or systemically. Topical administration is advantageously achieved with creams, ointments or lotions, or via aerosol introduction into the respiratory tract. Systemic administration may be orally, nasally, intrabronchially, parenterally or rectally. In each instance, conventional formulations amenable to use in the desired administration route is appropriate. Hence, tablets and capsules may be prepared for oral administration, suppositories for rectal administration, isotonic aqueous solutions for intravenous, subcutaneous of intramuscular injection and in aerosol suspensions for inhalation.

As is conventional in the use of antihistamine agents, the appropriate dosage is determined on a subjective basis for initial administration in small amounts, c.a. 0.5–15 mg., followed by increasing quantities up to about 400 mg., depending upon the desired route of administration, until the desired symptomatic relief is obtained. The dosage is personalized in this manner for each patient, based upon size, age, type of discomfort, degree of disability, etc., by the physician.

What is claimed is:

1. A compound of the formula

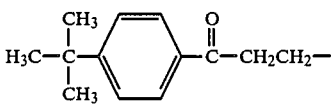

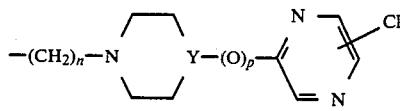

in which
- n is one of the integers 0, 1 or 2;
- p is one of the integers 0 or 1;
- Y is —N= or —CH=; with the proviso that when Y is —N=, p is zero, and when Y is —CH=, p is one;

or a pharmaceutically acceptable salt thereof.

2. The compound of claim 1 which is 1-[3-(tert-butylbenzoyl)propyl]-4-(6-chloro-2-pyrazinyl)piperazine or a pharmaceutically acceptable salt thereof.

3. The compound of claim 1 which is 4-[4-(3-chloro-2-pyrazinyl)-piperazinyl]-1-[4-(1,1-dimethylethyl)-phenyl]-1-butanone or a pharmaceutially acceptable salt thereof.

4. The compound of claim 1 which is 4-[4-(6-chloro-2-pyrazinyl)oxy]-1-piperidinyl-1-[4-(1,1-dimethylethyl]-phenyl]-1-butanone or a pharmaceutically acceptable salt thereof.

* * * * *